United States Patent
Heal et al.

(10) Patent No.: US 10,140,427 B2
(45) Date of Patent: Nov. 27, 2018

(54) METHOD AND SYSTEM FOR ANALYSIS OF COMPOUNDS

(75) Inventors: Richard D. A. Heal, Dorchester (GB); Alan T. Parsons, Dorchester (GB)

(73) Assignee: Midas Mediscience Limited, Sittingbourne (GB)

( * ) Notice: Subject to any disclaimer, the term of this patent is extended or adjusted under 35 U.S.C. 154(b) by 1227 days.

(21) Appl. No.: 10/551,070

(22) PCT Filed: Mar. 23, 2004

(86) PCT No.: PCT/GB2004/001228
§ 371 (c)(1),
(2), (4) Date: Sep. 27, 2005

(87) PCT Pub. No.: WO2004/088536
PCT Pub. Date: Oct. 14, 2004

(65) Prior Publication Data
US 2006/0177869 A1    Aug. 10, 2006

(30) Foreign Application Priority Data

Mar. 29, 2003  (GB) .................................. 0307352.5

(51) Int. Cl.
*G06F 19/00*  (2018.01)
(52) U.S. Cl.
CPC .......... *G06F 19/707* (2013.01); *G06F 19/706* (2013.01)
(58) Field of Classification Search
None
See application file for complete search history.

(56) References Cited

U.S. PATENT DOCUMENTS

| | | | |
|---|---|---|---|
| 5,772,983 A | 6/1998 | Grant et al. | |
| 5,981,268 A | 11/1999 | Kovacs et al. | |
| 6,377,057 B1 * | 4/2002 | Borkholder | 324/692 |
| 2001/0049689 A1 | 12/2001 | Mentzer | |
| 2002/0165674 A1 | 11/2002 | Bondarenko et al. | |
| 2002/0193673 A1 | 12/2002 | Fuller | |
| 2004/0175294 A1 | 9/2004 | Ellison et al. | |
| 2004/0204878 A1 | 10/2004 | Anderson et al. | |
| 2004/0265830 A1 * | 12/2004 | Szabo et al. | 435/6 |
| 2005/0014129 A1 * | 1/2005 | Cliffel et al. | 435/4 |

FOREIGN PATENT DOCUMENTS

| | | |
|---|---|---|
| JP | 10-170422 | 6/2010 |
| WO | WO 00/25255 | 5/2000 |
| WO | WO 00/65484 | 11/2000 |
| WO | WO 02/04943 | 1/2002 |
| WO | WO 03/017177 | 2/2003 |

OTHER PUBLICATIONS

Denyer et al., "Preliminary study on the suitability of a pharmacological bio-assay based on cardiac myocytes cultured over microfabricated microelectrode arrays", Medical and Biological Engineering and Computing, Sep. 1998, pp. 638-644.*
Sokal, David M. et al., "Multi-Neuronal Recordings Reveal a Differential Effect of Thapsigargin on Bicuculline- or Gabazine-Induced Epileptiform Excitability in Rat Hippocampal Neuronal Networks", NeuroPharmacology, vol. 39, No. 2, Jan. 1, 2000, pp. 2408-2417 (10 Pages).
Denyer et al., "Preliminary Study on the Suitability of a Pharmacological Bio-Assay Based on Cardiac Myocytes Cultured Over Microfabricated Microelectrode Arrays", Medical and Biological Engineering and Computing, Sep. 1998, pp. 638-644 (7 Pages).

* cited by examiner

*Primary Examiner* — Jason M Sims
(74) *Attorney, Agent, or Firm* — Brown Rudnick LLP

(57) ABSTRACT

The analysis of compounds utilising the physical response of cellular networks is described. Typically, the electrical characteristics of the cellular network are monitored although other characteristics such as fluorescence may be monitored. In any event, the analysis utilises signal processing techniques to derive a set of features which may be evaluated against a library of known responses. The technique may be applied to both the detection and identification of unknown compounds and the detection of concentrations of known compounds.

10 Claims, 8 Drawing Sheets

Fig.6.

| Program | Feature No. | Name | Description | Type of t-test |
|---|---|---|---|---|
| spike_rate | 1 | isr | instantaneous spike rate | unpaired |
| spike_rate | 2 | isrv | instantaneous spike rate variability | unpaired |
| spike_speed | 3 | ss | spike speed | unpaired |
| spike_speed | 4 | ssv | spike speed variability | unpaired |
| max_min | 5 | maxv | peak level | paired |
| max_min | 6 | minv | trough level | paired |
| max_min | 7 | rangev | peak-to-trough level | paired |
| max_min | 8 | maxmodv | absolute peak level | paired |
| rise_times | 9 | rise10_time | rise time from 10% of peak | paired |
| rise_times | 10 | rise20_time | rise time from 20% of peak | paired |
| rise_times | 11 | recov10_time | recovery time to 10% of peak | paired |
| rise_times | 12 | recov20_time | recovery time to 20% of peak | paired |
| rise_times | 13 | diffv | peak-to-trough time | paired |
| rise_times | 14 | qt | time from 3% and 97% of absolute profile area | paired |
| rise_times | 15 | dec_mpt | decay rate of profile tail | paired |
| spike_area | 16 | mean_abs | absolute profile area | paired |
| spike_area | 17 | mean_rise | profile rise area | paired |
| spike_area | 18 | mean_abs_recov | absolute profile recovery area | paired |
| moments | 19 | mom | turning moment of profile | paired |
| moments | 20 | cog | centre of gravity of absolute profile | paired |
| moments | 21 | rog | radius of gyration of absolute profile | paired |
| spectrum | 22 | varv | amplitude variance | paired |
| spectrum | 23 | maxspec | maximum power spectral value | paired |
| spectrum | 24 | locmaxspec | frequency of maximum power spectral value | paired |
| spectrum | 25 | spec1 | amplitude variance (normalised) in band 1 | paired |
| spectrum | 26 | spec2 | amplitude variance (normalised) in band 2 | paired |
| spectrum | 27 | spec3 | amplitude variance (normalised) in band 3 | paired |
| specrtum | 28 | spec4 | amplitude variance (normalised) in band 4 | paired |
| spectrum | 29 | spec2re1 | amplitude variance band 2 relative to band 1 | paired |
| spectrum | 30 | swpec3re2 | amplitude variance band 3 relative to band 2 | paired |
| spike_hos | 31 | ccv | amplitude correlation coefficient | 1-sided |
| spike_hos | 32 | skew | amplitude skewness (normalised) | paired |
| spike_hos | 33 | kurt | amplitude kurtosis (normalised) | paired |
| entropy | 34 | ent | entropy of profile | paired |
| entropy | 35 | enta | entropy of absolute profile | paired |
| wavelets | 36 | wmaxv | maximum wavelet transform coefficient | paired |
| wavelets | 37 | scale_maxmaxv | scale of wavelet transform coefficient | paired |
| wavelets | 38 | wvv | variance of wavelet transform | paired |
| wavelets | 39 | wtrfv | wavelet transform transfer coefficient | unpaired |
| wavelets | 40 | wvmv | variance of wavelet transform ridge values | paired |
| wavelets | 41 | wtrfmv | wavelet transform ridge value transfer coefficient | unpaired |

METHOD AND SYSTEM FOR ANALYSIS OF COMPOUNDS

BACKGROUND OF THE INVENTION (1) Field of the Invention

The present invention relates to the analysis of compounds, particularly, although not exclusively chemical compounds utilised in the healthcare, pharmaceutical, cosmetic and environmental sectors.

(2) Description of the Art

It has become the case that in the search for ever more effective pharmaceutical compounds an ever-increasing amount of time, effort and resources have been devoted to identifying and isolating potentially beneficial chemical compounds. Traditionally, the approach has been to select a molecular target within a biochemical pathway, such as an enzyme or a receptor where interaction with the target by a compound could lead to changes which treat the disease. Typically, the interaction would take the form of the compound inhibiting or exciting the pathway. Clearly, a large number of targets will be under investigation at any one time. In order to evaluate the target against potentially useful compounds it is necessary to produce samples of the target for testing, typically through a cloning process. The target is then screened in a series of tests against these compounds with a view to eliminating those compounds which are unsuitable and to identify those compounds that are potentially valuable. It is sometimes the case that there may be sufficient biostructural information on the molecular target to suggest the design of potentially valuable compounds. Even so, for the most part hundreds of thousands of compounds are typically screened using robotic technology. Typically, the entire process from initial selection of a target through to the identification of candidate compounds can take several years.

Once identified as potentially of value in this first screening phase, compounds showing the appropriate activity are subjected to further screens with the aim of determining their level of potency and selectivity for the target. From these data, leads will be identified.

Once a potential candidate compound has been identified, it is then subjected to further development including more screening to meet the needs of various studies both clinical and non-clinical studies. The biological effects of a compound will be assessed, wherever possible avoiding using animals in safety testing. Thus, cells in culture are an attractive alternative for the basis for such investigations. Increasingly automation is being applied to such assessment and whilst for the most part conventional assaying techniques are utilised there has been some initial attempts at employing automated techniques.

One such technique which has been applied to the analysis of cell culture in response to a compound is that set out in U.S. Pat. No. 6,377,057 which describes a technique and apparatus for classifying biological agents according to the spectral density signature of evoked changes in cellular electric potential. It is suggested in the Patent that the approaches it teaches are intended to go beyond those previous attempts to measure cellular electric potential. Such early attempts have, it is suggested, produced output more suited to interpretation by an experienced neuroscientist. Indeed, although such tools have been available to researchers and expert practitioners such as cardiologists since the early 1970's, it is suggested that the invention disclosed in the Patent is intended to be of more general use. As such the patent discloses a relatively unsophisticated analysis mechanism based on interpreting the power spectral density (PSD) of a cellular response. Thus, whilst the Patent teaches that the technique is capable of identifying unknown compounds and determining the characteristics of compounds, analysis based purely on the spectral density changes of such evoked membrane potential or action potential is considered to limit the value of the results obtained in the interests of reducing the complexity of analysis.

SUMMARY OF THE INVENTION

According to a first aspect of the invention, there is provided a compound analysis method: this method comprises determining a vector quantity having a number of dimensions equal to a number of features derived from the electrical output of an electrically active cellular network, with each component of said vector being representative of a change in said feature resulting from the application of a compound to said electrically active cellular network and classifying said vector in accordance with a predetermined cluster analysis methodology.

When stimulated, cellular activity may change. By analysing the changes in the signal and comparing with a library of pre-determined behavioural features, the stimulus can be characterised and/or the impact on the cellular network quantified. Using processing algorithms based on those currently used for sonar signal processing, signal features can be related to molecular events occurring within the cellular structure. Such features may be electrical, chemical or fluorescent in nature, the requirement being that a suitable transducer is provided.

According to another aspect of the invention, there is provided a compound analysis system, the system comprising a micro-electrode array provided by a bio-compatible substrate having a plurality of electrodes situated thereon, said electrodes having an arrangement on said substrate corresponding substantially to that of an electrically active cellular network disposable in use thereon a multi-channel amplifier coupled to said electrodes and an analyser operatively connected to said amplifier to determine for each active channel a vector quantity having a number of dimensions equal to a number of features derived from the electrical output of said electrically active cellular network with each component of said vector being representative of a change in said feature.

Conveniently, the system may be used for the testing of blood/urine samples for drugs. A particular application may be to test for performance enhancing drugs in athletes or for patient compliance.

The delivery of a compound to the system may be placed under the control of a perfusion system. By utilising such a perfusion system it is possible to be more confident that accurate delivery of a compound, such as a drug takes place. A perfusion system allows correct and potentially varying doses of the drug, to be delivered at a know time. Furthermore, the perfusion system may ensure that the drug is added at the correct temperature with a controlled and smooth delivery.

Thus, the system is particularly suitable for the needs of the pharmaceutical market, in that it may identify and quantify behavioural changes in the cellular structure when exposed to external stimuli. Conveniently, post-processing activities could include comparison with a pre-determined library of responses to identify the stimulator, or a simple output to determine whether the reaction falls within acceptable limits According to a still further aspect of the invention, there is provided a compound analysis apparatus, the apparatus including a processor and a memory, the processor being operable in response to signals derived from a micro-electrode array connected, in use, thereto, to determine a vector quantity having a number of dimensions equal to a number of features derived from the electrical output of said micro-electrode array with each component of said vector being representative of a change in said feature, wherein said memory contains a library of features characterising known compounds such that classification of said vector enables identification of a compound deposited, in use, on said array, in accordance with a predetermined measure of statistical reliability.

The signals derived from the micro-electrode array although electrical in nature may originate from not only electrical activity but also other changes in the physical characteristics of a cellular network deposited, in use, on the array. Clearly, there is a requirement that a transducer on or in proximity to the array is capable of providing electrical signal representative of the characteristics being monitored.

According to still another aspect of the invention, there is provided a sensor for compound detection, the sensor comprising a receptacle for a micro-electrode array, said receptacle having a connector for receiving electrical signals from said array when received in said receptacle, an amplifier for amplifying said signals and a processor, the processor being operable in response to said signals to determine a vector quantity having a number of dimensions equal to a number of features derived from the electrical output of said micro-electrode array with each component of said vector being representative of a change in said feature.

Such a sensor may be packaged to suit a variety of applications such as, but not exclusively, water quality analysis, environmental monitoring and process control in, for example, the production of pharmaceuticals, cosmetics, foodstuffs and the like.

In general, once a set of baseline measurements from an array has been recorded, any change in cellular behaviour can be identified and quantified. Such changes may be induced through exposure to a stimulus. In the embodiments of the invention set out below, the stimulus would be in the form of a chemical compound.

Optionally, an automated perfusion system may facilitate delivery of drug compounds to the cellular network in a smooth and controlled manner.

DESCRIPTION OF THE FIGURES

In order to understand more fully the invention, a number of embodiments thereof shall now be described by way of example and with reference to the accompanying drawings, in which:

FIG. 6 is a table illustrating a feature set selected for use with the invention;

DESCRIPTION OF A PREFERRED EMBODIMENT

Figure 1:
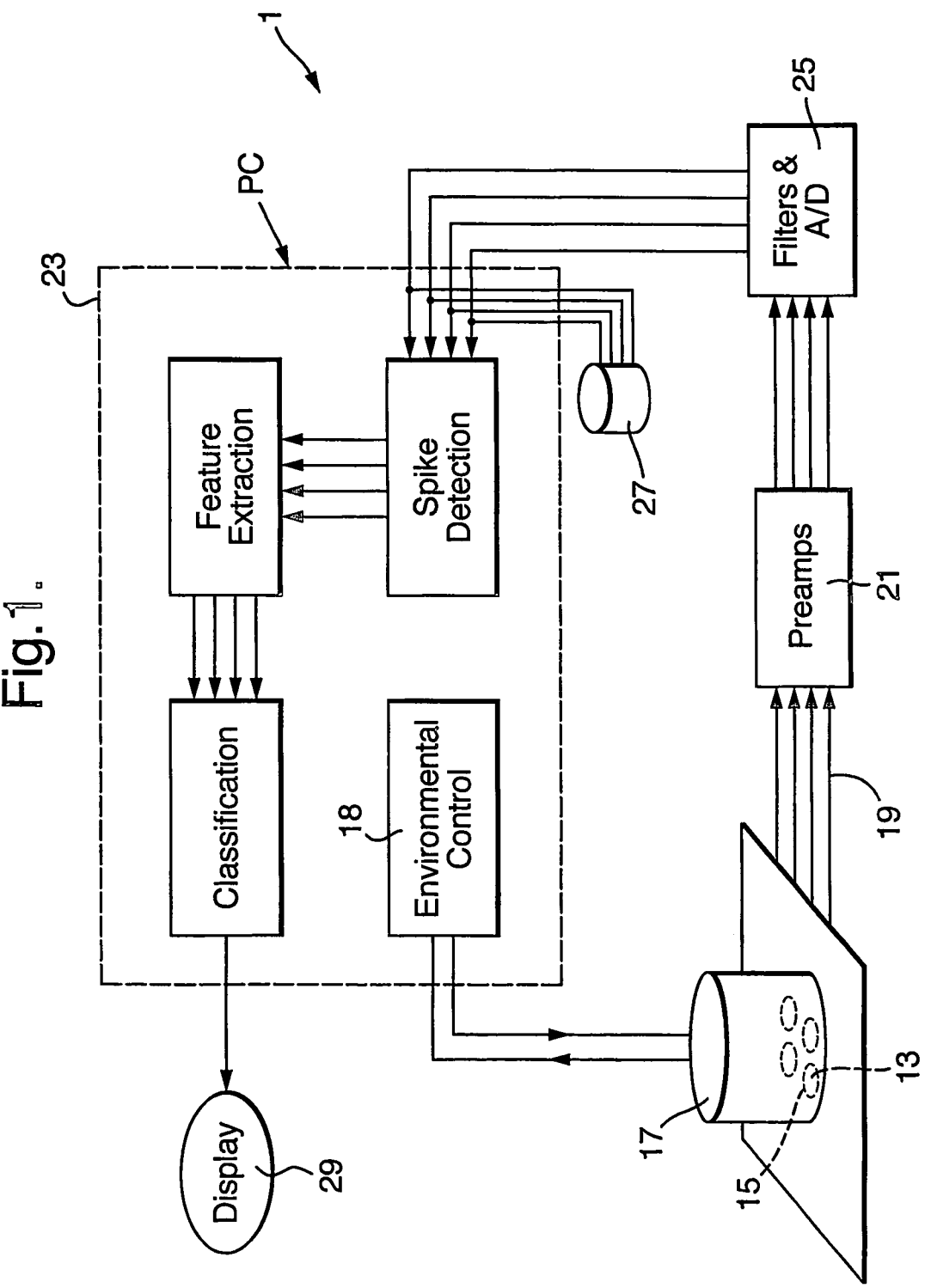
FIG. 1, is a diagrammatic view of an analysis system in accordance with one aspect of the present invention.

With reference to the Figures and FIG. 1, in particular, there is shown an analysis system 1 in which an MEA 3 (see FIG. 2) provides a site onto which a cellular network is deposited. The nature of the cellular network is described in respect of a particular example below, namely a network made up of a plurality of cardio-myocytes. However, it will be appreciated from the outset by those skilled in the art that this particular example of a cellular network is purely exemplary and any reference to cellular network should not be taken to mean purely the example 5 cited herein.

Figure 2:
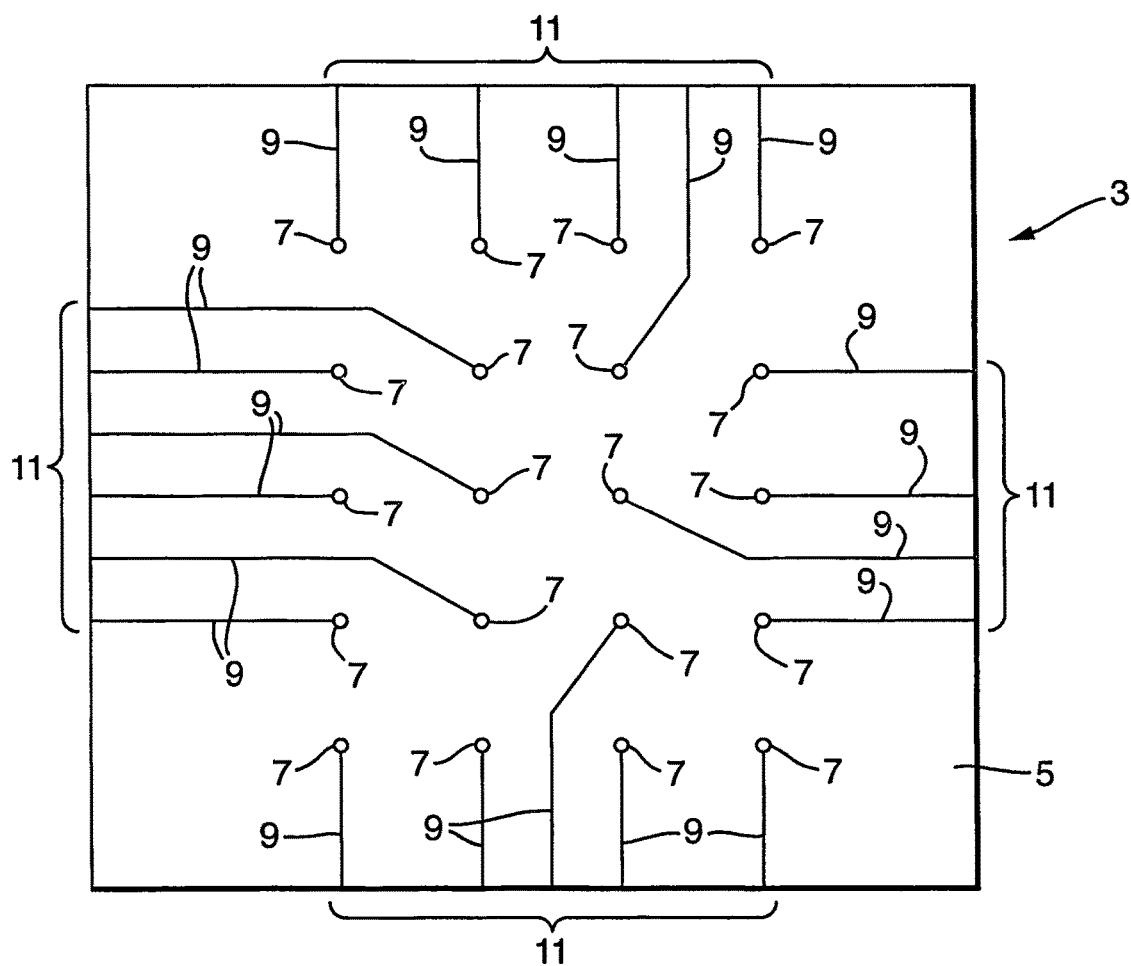
FIG. 2, is plan view of a micro-electrode array (MEA) forming part of the system of FIG. 1.

The MEA 3 comprises a bio-compatible substrate 5 on which are surface mounted a plurality of electrodes 7 each of which is connected by traces 9 to an edge connector 11. The MEA 3 is insertable within a receptacle 13 formed at the bottom of a well 15. The receptacle 13 is provided with contacts for the edge connector 11. The well 15 is hermetically sealed and forms the environment or chamber 17 within which a compound is analysed. The chamber is itself connected via a ribbon connector 19 to the input of an amplifier unit 21. The combination of the edge connector 11 and receptacle 13 provides for easy insertion and removal of MEAs 3 for analysis of different compounds. Although FIG. 2 illustrates a square array made up of equidistant electrodes, alternative array layouts are contemplated having, for example, non-uniform electrode pitch and layout. The adoption of a particular layout is predicated on the requirement that an electrode 7 should be capable of detecting electrical activity from a single cell in a network when arranged on the MEA 3. Clearly, the packing or form factor of the MEA 3 must be such that it can be correctly and easily inserted and removed from the receptacle 13 in the well 15.

Output from each electrode 7 passes via the aforementioned cable interconnect 19 to the amplifier unit 21 where the output is amplified. The amplifier unit 21 is a multi-channel device capable of providing a gain of around 1000 to each channel. Typically, sufficient channels are available to allow each electrode 7 of the MEA 3 to be mapped to a channel. Depending on the configuration of the MEA 3 there may be need for more or less channels for satisfactory data collection. The amplifier unit 21 itself is interfaced to a PC-based data acquisition system 23. The PC system 23 incorporates an Analogue to Digital conversion card 25 coupled via a PCI bus to a central processor unit. The card 25 provides the external connections necessary to interface the analogue output of the amplifier 21 to the acquisition system 23. The card 25 is capable of sampling the amplified channel data from the amplifier unit 21 at up to 50 kHz/channel. The central processor unit carries out instructions provided by software and/or firmware necessary to analyse the digitised data. The data may be analysed in real time as events occur on the MEA 3 or retrieved later from a storage device 27 such as a hard disk. In the former case, the storage device 27 may still be utilised to archive the data for later repeated or further analysis. The ability to proceed with real time as opposed to or off-line analysis will in some part depend on the rate at which data is generated and the storage capacity of the system 23. The nature of the cellular network placed on the MEA 3 determines the sampling rate. Thus the software and/or firmware is provided with logic to enable the system 23 to operate at an optimum sampling rate for the particular cellular network taking into account any limitations of processor speed and storage capacity. Thus, in the case of a cellular network made up of cardio-myocytes, activity may occur relatively slowly over a 100 mS window whereas in the case of neurones, activity may be present in much shorter windows of around 15 to 25 mS. In the former case, a relatively lower sampling rate may be adopted by the system 23, with the relevant control signals being provided to the Analogue to Digital Converter 25, than is needed for equivalent resolution of detail in the data derived from a neurone network. The PC system 23 is provided with a VDU 29 and printer for the presentation of results.

Figure 3:
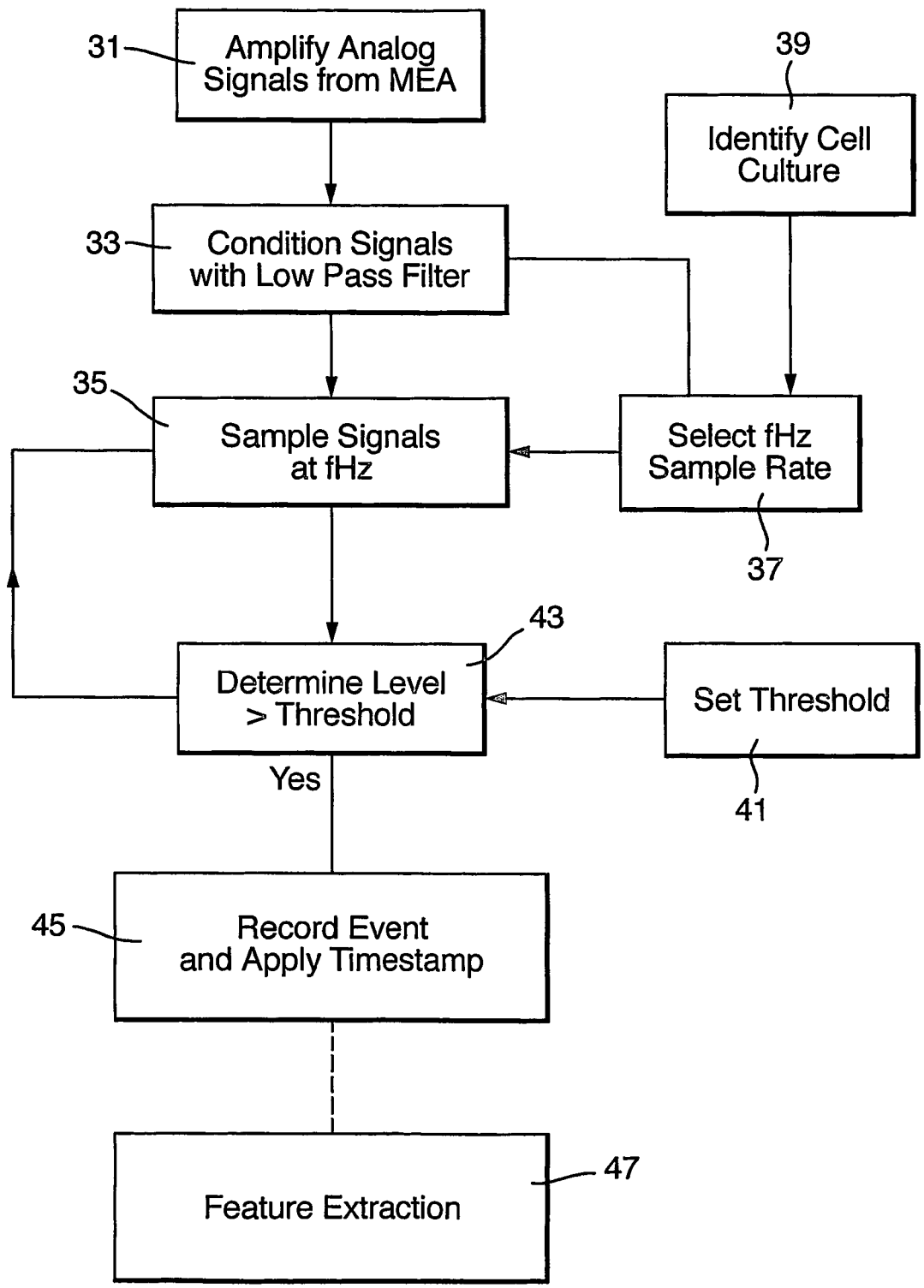
FIG. 3, is a flow chart indicative of a method of analysis in accordance with a further aspect of the present invention.

In use, and referring especially to FIG. 3 again figure of the order of 1000 is applied to each analogue channel which, in the example whose preparation is described below, namely a cardio-myocyte cellular network, has a pre-amplification value of around 100 microvolts to 2 millivolts. At this stage, the output from the electrodes 7 on the MEA 3 is an analogue signal. Clearly, before digital signal processing can be applied there is a need to digitise the signal. The rate at which the analogue signal is sampled must be selected to be high enough to ensure that all the features of interest in the electrical activity of a cellular network deposited on the MEA 3 are available to the digital signal processing unit. As a first step, the signals are amplified 31 and, the analogue signal from each electrode 7 is conditioned 33, in this case by low pass-filtering to remove unwanted high-frequency components. The filtered analogue signal on each channel is sampled 35 at a rate which may be as much as 50 kHz the actual rate 37 depending 39 on the nature of the cellular network placed on the MEA 3. In the case of a cardio-myocyte network, an effective sampling rate has been found to be 10 kHz.

By selecting a sampling rate of 10 kHz in the example of a cardiac myocyte cellular network, sufficient resolution is achieved without excessive data collection. For long-term recordings greater than 1 minute in duration, data may be stored as a series of 'cut-outs' of the electrical activity from the cardiac myocyte cells. Each cellular event stored as a 'cut-out' is determined by setting 41 a threshold level (usually a positive value) of at least 2 root-mean-square values of the noise above the baseline. For each event, a time stamp is recorded at the point at which the threshold level is crossed 43. In addition, electrode raw data 15 msec before and 85 msec after the threshold level has been crossed is stored. Data is saved to a file on the hard disk in a mcd file format (approximately 10 Mb per electrode for a 60 second recording).

The data stored on the hard disk is representative of the changes in electrical activity that occur within a cellular network and are typically in the form of action potentials or spikes. As will be described further below changes occur to the shape of the spikes and their temporal and spatial pattern when a compound is introduced to a cellular network. The electrical activity data from the cellular network is analysed in software by imposing temporal and spatial information onto a model of the electrode array. In this way, both local and global properties of the electrical activity across the tissue sample can be identified and quantified. Examples of local properties are the peak height, amplitude or depolarisation time of an action potential detected at an individual electrode. Examples of global properties are the beat frequency and propagation speed of action potentials across the culture. These various properties are referred to as features. The process of feature extraction 47 may then be performed on this digitised data.

In a variant of the present embodiment, before data is stored in a datafile, the features themselves may be used to reduce the requirements for data storage. Thus the spikes can first be identified using a threshold detector, catalogued and stored, the rest of the data being ignored. Since the temporal length of a spike is typically much less than the time separation between spikes this procedure requires less storage capacity.

A non-exhaustive set of features identifiable by the analysis system 23 is listed below.

Examples of Features

Mean Spike Rate—the number of spikes observed in a channel divided by the record length. The mean spike rate feature may be updated every minute or few minutes rather than over the whole course of an experiment.

Spike Rate Variability—calculated from the time differences between consecutive spikes, averaged over all channels.

Spike Speed—the propagation speed of the spike pulse across the MEA plate, calculated for each pulse from the spike time arrivals at each selected channel using a least mean squares fit to the data on the assumption of a single plane wave pulse propagating with constant speed.

Arrival Angle—the direction of propagation of the spike pulse.

Increase In Peak Level—the relative increase between control and test data in the maximum level of the spike profile averaged over all spikes and all selected channels.

Increase in Trough Level—the relative increase between control and test data in the minimum level of the spike profile averaged over all spikes and all selected channels.

Increase in Peak-to-Trough Level—the relative increase in the range of spike profile averaged over all spikes and all selected channels.

Increase in Absolute Peak Level—the relative increase in the maximum absolute level of the spike profile averaged over all spikes and all selected channels.

Increase in Rise Time from 10%—the relative increase in the time for a spike to achieve its maximum level starting from a level of 10%/o of the maximum, averaged over all spikes and all selected channels.

Increase In Rise Time from 20%—the relative increase in the time for a spike to achieve its maximum level starting from a level of 20% of the maximum, averaged over all spikes and all selected channels Increase in Recovery Time to 10%—the relative increase in the time for a spike to recover to 10% of its minimum value starting from the minimum value, averaged over all spikes and all selected channels Increase In Recovery Time to 20%—the relative increase in the time for a spike to recover to 20% of its minimum value starting from the minimum value, averaged over all spikes and all selected channels Increase in Peak-to-Trough Time—the relative increase in the time between the maximum level and the minimum level in a spike profile, averaged over all spikes and all selected channels.

Increase In Absolute Profile Area—the relative increase in the area under the modulus profile, averaged over all spikes and all selected channels.

Increase In Profile Rise Area—the relative increase in the area under the profile between the start and the maximum value, averaged over all spikes and all selected channels.

Increase in Profile Recovery Area—the relative increase in the area under the profile between the minimum value and the end, averaged over all spikes and all selected channels.

Increase In Absolute Profile Recovery Area—the relative increase in the area under the modulus profile between the minimum value and the end, averaged over all spikes and all selected channels.

Increase in Profile Correlation Coefficient—the normalised cross-correlation between the control and test spike profiles, averaged over all spikes and all selected channels.

Increase in Profile Variance—the relative increase in the variance of the spike profile, averaged over all spikes and all selected channels.

Increase in Profile Skewness—the relative increase in the skewness of the spike profile, averaged over all spikes and all selected channels.

Increase in Profile Kurtosis—the relative increase in the kurtosis of the spike profile, averaged over all spikes and all selected channels.

Increase in maximum of wavelet transform—the relative increase in the maximum value over scale and time delay of the wavelet transform of the spike profile, using for example a Daubechies wavelet of order 2 here and below, averaged over all spikes and all selected channels.

Increase in variance of wavelet transform—the relative increase in the variance of the wavelet transform values of the spike profile, summed over scale and time delay, averaged over all spikes and all selected channels.

Wavelet cross-correlation coefficient—the normalised cross-correlation in scale and time delay between the wavelet transforms of the control and test spike profiles, averaged over all spikes and all selected channels.

Increase in wavelet transform transfer coefficient—similar to the wavelet cross-correlation coefficient, except that it is normalised by the autocorrelation of the wavelet transform of the control data, instead of by the square root of the product the autocorrelation of the wavelet transform of the control data and the autocorrelation of the wavelet transform of the test data.

Increase in profile entropy—the relative increase in the entropy of the spike profile as determined from its histogram, averaged over all spikes and all selected channels.

Another feature set which is believed to particularly effective in forming the basis for analysis is set out below and repeated in tabular form as FIG. 6 of the drawings. This feature set provides a numerical description of the various changes in the heart beat profile when a drug is applied Instantaneous Spike Rate—the relative increase between control and test data in the instantaneous spike rate averaged over all selected channels.

Instantaneous Spike Rate Variability—the relative increase between control and test data in the temporal variability of the instantaneous spike rate.

Spike Speed—the relative increase between control and test data in propagation speed of the spike pulse across the MEA plate, calculated for each pulse from the spike time arrivals recorded at each selected each channel.

Spike Speed Variability—the relative increase between control and test data in the temporal variability of the spike speed.

Peak Level—the relative increase between control and test data in the maximum value in the averaged spike profile obtained by averaging the profiles of all the spikes in each selected channel.

Trough Level—the relative increase between control and test data in the minimum value in the averaged spike profile obtained by averaging the profiles of all the spikes in each selected channel.

Peak-to-Trough Level—the relative increase between control and test data in difference between the maximum and minimum values in the averaged spike profile obtained by averaging the profiles of all the spikes in each selected channel.

Absolute Peak Level—the relative increase between control and test data in the maximum value in the absolute averaged spike profile obtained by averaging the profiles of all the spikes in each selected channel.

Rise Time to 10%—the increase between control and test data in the time for an averaged spike to achieve its maximum level starting from a level of 10% of the maximum.

Rise Time to 20%—the increase between control and test data in the time for an averaged spike to achieve its maximum level starting from a level of 20% of the maximum.

Recovery Time to 10%—the increase between control and test data in the time for an averaged spike to recover to 10% of its minimum level.

Recovery Time to 20%—the increase between control and test data in the time for an averaged spike to recover to 20% of its minimum level.

Peak-to-Trough Time—the increase between control and test data in the time between the maximum level and the minimum level in the averaged spike profile.

QT Time—the increase between control and test data in the time between the 3% and 97% cumulative points of the absolute area under the averaged spike profile.

Profile decay rate—the increase between control and test data in the decay rate of the tail of the averaged profile.

Absolute Profile Area—the relative increase between control and test data in the area under the modulus of the avaereged profile.

Profile Rise Area—the relative increase between control and test data in the area under the averaged profile between the start and the maximum value.

Absolute Profile Recovery Area—the relative increase between control and test data in the area under the modulus of the averaged profile between the minimum value and the end.

Profile turning moment—the relative increase between control and test data of the temporal turning moment of the averaged profile.

Absolute profile centre of gravity—the relative increase between control and test data of the centre of gravity of the absolute averaged profile.

Absolute profile radius of gyration—the relative increase between control and test data of the radius of gyration of the absolute averaged profile measured about its centre of gravity.

Amplitude Variance—the relative increase between control and test data in the variance of the averaged spike profile.

Maximum spectral value—the relative increase between control and test data in the maximum value of the power spectrum of the averaged spike profile.

Frequency of maximum spectral value—the relative increase between control and test data in the frequency of the maximum value of the power spectrum of the averaged spike profile.

Amplitude Variance in Frequency Band 1—the relative increase between control and test data in the variance of the averaged spike profile, normalised by the total variance, in the frequency band 0-250 Hz.

Amplitude Variance in Frequency Band 2—the relative increase between control and test data in the variance of the averaged spike profile, normalised by the total variance, in the frequency band 250-500 Hz.

Amplitude Variance in Frequency Band 3—the relative increase between control and test data in the variance of the averaged spike profile, normalised by the total variance, in the frequency band 500-750 Hz.

Amplitude Variance in Frequency Band 4—the relative increase between control and test data in the variance of the averaged spike profile, normalised by the total variance, in the frequency band 750-1000 Hz.

Amplitude Variance in Band 2/Band 1—the relative increase between control and test data in the ratio of the variances in bands 2 and 1 in the spectrum of the averaged spike profile.

Amplitude Variance in Band 3/Band 2—the relative increase between control and test data in the ratio of the variances in bands 3 and 2 in the spectrum of the averaged spike profile.

Amplitude Correlation Coefficient—the normalised cross-correlation between the averaged control and averaged test spike profiles.

Amplitude Skewness (normalied)—the relative increase between control and test data in the skewness, normalised with respect to the total variance, of the averaged spike profile.

Amplitude Kurtosis (normalied)—the relative increase between control and test data in the kurtosis, normalised with respect to the total variance, of the averaged spike profile.

Entropy of profile—the relative increase between control and test data in the entropy of the averaged spike profile as determined from its histogram.

Entropy of absolute profile—the relative increase between control and test data in the entropy of the absolute averaged spike profile as determined from its histogram.

Maximum wavelet transform coefficient—the relative increase between control and test data in the maximum value over scale and time delay of the wavelet transform of the averaged spike profile, using a Daubechies wavelet of order 2 here and below.

Scale change of wavelet transform coefficient—the relative increase between control and test data in the scale of maximum value over scale and time delay of the wavelet transform of the averaged spike profile, using a Daubechies wavelet of order 2 here and below.

Variance of wavelet transform—the relative increase between control and test data in the variance of the wavelet transform values of the averaged spike profile, summed over scale and time delay.

Wavelet transform transfer coefficient—wavelet cross-correlation coefficient normalised by the autocorrelation of the wavelet transform of the control data.

Variance of wavelet transform ridge values—the relative increase between control and test data in the variance of the vector of wavelet transform values of the averaged spike profile obtained by taking the maximum value at each scale.

Wavelet transform transfer coefficient ridge values—wavelet cross-correlation coefficient of the maximum vector as defined above, normalised by the autocorrelation of the corresponding vector in the control data.

It should be noted that not all the above features are amplitude dependant. Thus, features which depend on the recovery rate of the cellular network may be used to assist in detection and classification. Furthermore, although the above features may or may not be present to a greater or lesser extent in the electrical activity of the cellular network it is considered that similar features may be identified from the chemical behaviour of the network in respect of its fluorescent and/or luminescent activity.

Figure 7:
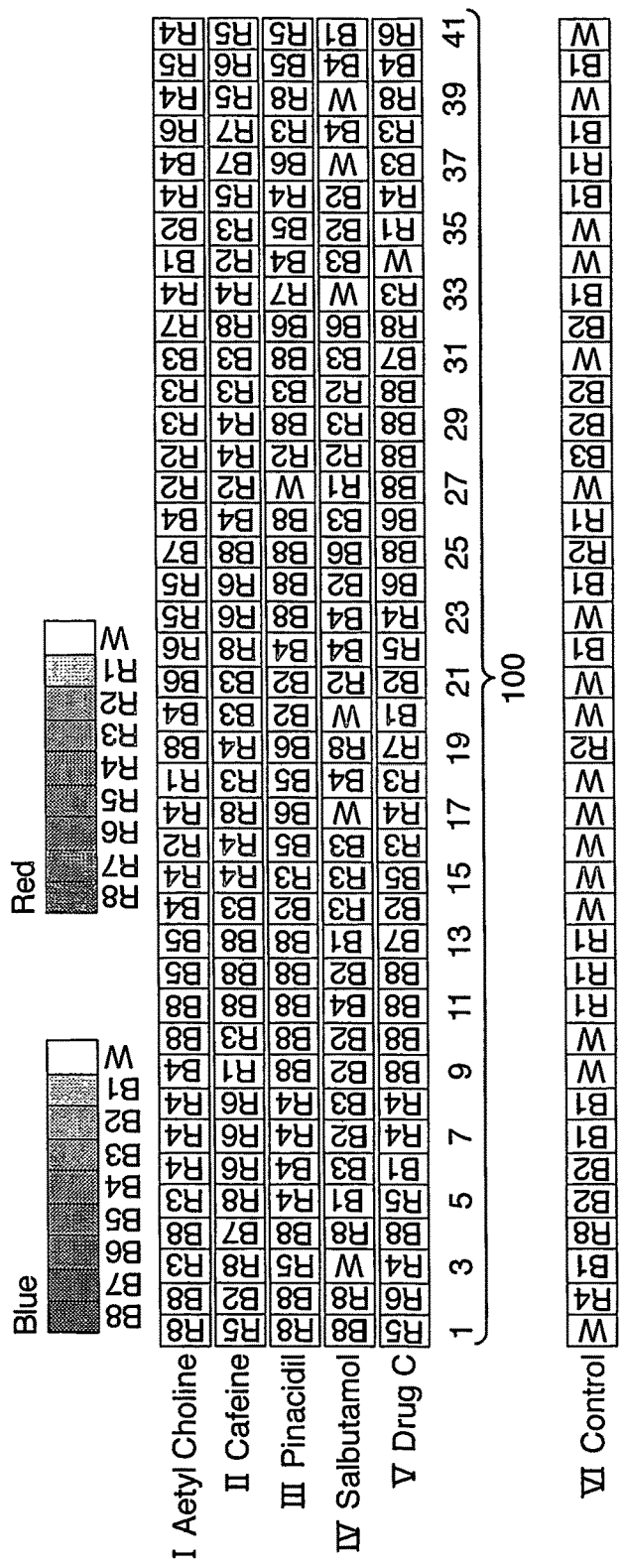
FIG. 7 is a matrix indicative of a set of responses across a feature set for example compounds in accordance with the invention.

FIG. 7, exemplifies the results of a feature set analysis in a matrix format for a set of different compounds aetyl choline I, cafeine II, pinacidil III, salubutamol IV and drug C V, such as might result from carrying out activities set out in the examples below. The numerals 100 beneath the columns are indicative of respective features in a feature set and the level of shading of the boxes indicates the nature of the response. Results from a control VI are shown separately.

Figure 8:
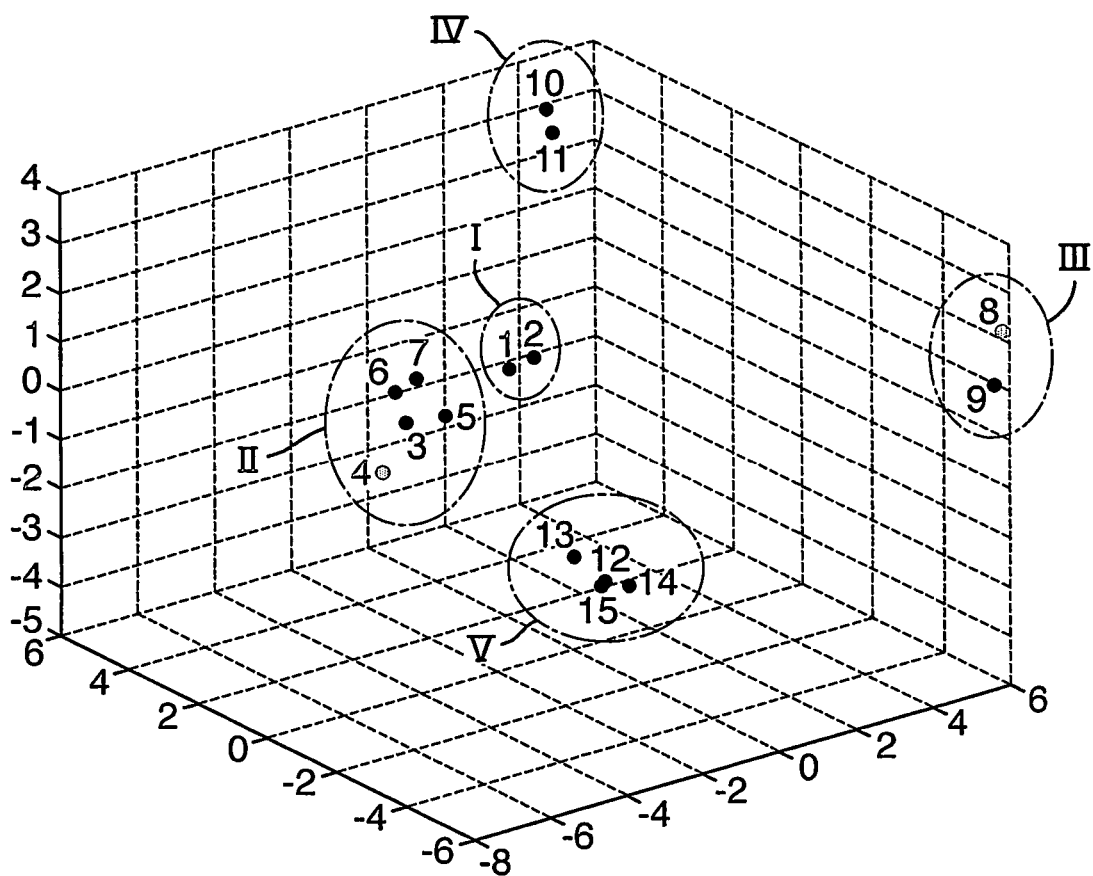
FIG. 8 is a vector diagram based on the responses of FIG. 7.

FIG. 8 shows the outcome of plotting the results of a feature set as a vector quantity in three-dimensional space for the compounds of FIG. 7 where clustering of the results is evident for each of the compounds identified by their respective reference numerals.

The sequence of activities necessary to analyse a compound is set out below. These activities are a combination of physical processes taken in relation to the deposition of a cellular network on the MEA and the compound to be tested together with signal processing activity which is carried out utilising the PC-based system 23. Firstly a cellular network is cultured and deposited on the MEA 3. An example of the steps required in this regard using cardio-myocyte cells is as follows:

EXAMPLE (a) heart tissue is isolated from rat embyos (E15-E18) or neonates.
(b) The heart tissue is minced using a scalpel and placed into cold (4° C.) $Ca2+/Mg2+$—free Hanks balanced salt solution (HBSS)
(c) The tissue is washed (3 times) in fresh HBSS and replaced with 0.05% trypsin in HBSS
(d) Incubate 10 mins at 37° C. and discard supematant
(e) Fresh DNase type II solution added (10,000 Units/ml) for 2 mins
(f) Fresh trypsin added and incubated at 37° C. for 8 mins
(g) Supernatant removed and placed into HAMS F10 containing 36% FCS, 0.5% insulin/transferrin/selenite, 6 mM L-glutamine and 2% penicillin/streptomycin (200 mM stock)
(h) Cells are collected from suspension (1500 rpm, 5 mins) and resuspended in HAMS F10 containing 10% FCS, 0.5% insulin/transferrin/selenite, 6 mM L-glutamine and 2% penicillin/streptomycin (200 mM stock)
(i) Steps (e)-(h) repeated 5-8 times
(j) Differential adhesion is performed by incubating pooled cell suspensions in a treated tissue culture flask for 2 hrs at 37° C.
(k) The final cell suspension is counted and seeded onto fibronectin treated MEA plates at 50K per plate in a 100 μl volume.

The cell suspension is deposited on the MEA 3 such that each electrode 7 is in contact with a respective cell.

Once the cellular network is in place on the MEA 3, the MEA 3 is inserted within the receptacle 13 in the well 15 such that a set of baseline measurements may be recorded. Accordingly, the analogue output from the electrodes 7 is amplified 31, filtered 33 and stored 45 utilising the equipment and methodology set out above. Throughout this baseline assessment stage and subsequently during the analysis of a compound, it is desirable to maintain the cell culture conditions substantially constant. Thus, the environment is monitored utilising sensors deployed in the cell culture chamber 17 encompassing the MEA. The sensor output is monitored by a software module 18 running on the PC-based data acquisition system 23 or it may be monitored independently. In either case, the signals received form the sensor are employed to adjust environmental controls. The parameters which may be monitored could include temperature, pH and dissolved oxygen concentration of the culture medium.

The recording process for the baseline measurements is performed for each data channel corresponding to an electrode 7. For a given record (typically 100 seconds long) a set of so-called healthy channels is identified as follows by identifying the set of channels with the most frequently occurring non-zero number of spikes.

A compound to be analysed is then introduced to the cellular network covering the MEA 3. This may be applied directly to the network on the MEA 3 used for baseline assessment or a further equivalent sample of cultured network may be prepared on a further MEA 3 and inserted in the receptacle 13 in the well 15 in its place. Again, for a given record (typically 100 seconds in duration although a longer or shorter period may be selected) a set of so-called healthy channels is selected by identifying the set of channels with the most frequently occurring non-zero number of spikes. The healthy channels in each set i.e. the baseline measurements and the subsequent measurements in the presence of the compound are then compared further to identify the channels which are common to both sets. These common channels are then subjected to feature extraction to form a feature set.

To be useful in the subsequent detection and classification stages, a feature must be readily extractable from the data and numerically quantifiable. Various processing algorithms are used to extract features meeting this requirement. As many such features as possible are included in the set to encompass as much of the information content of the data as possible. The presence of redundant features in the set is tolerated. Furthermore, by averaging as late as possible in the process, the sensitivity of the features is found to be enhanced. The significance of a measured feature can also be estimated by calculating the standard deviation of that measure over all the selected channels.

The feature set can then be viewed as a vector quantity, with dimensions equal to the number of features; each component representing the numerical change to the feature in question equal to the difference between the baseline and subsequent measurements. Detection and classification reduces to performing manipulations on the response vectors. The detection process has been described above. The classification process is achieved by the use of standard cluster analysis by which is to be understood those mathematical clustering and partitioning techniques which can be used to group cases on the basis of their similarity over a range of variables e.g. component. Many clustering algorithms are available; they differ with respect to the method used to measure similarities (or dissimilarities) and the points between which distances are measured. Thus, although clustering algorithms are objective, there is scope for subjectivity in the selection of an algorithm. The most common clustering algorithms are polythetic agglomerative, i.e. a series of increasingly larger clusters are formed by the fusion of smaller clusters based on more than one variable. This hierarchical approach is particularly suited to computer based analysis in view of the large data sets which are to be analysed. However, a less computationally intensive and therefore more rapid approach is the non-hierarchical k means, or iterative relocation algorithm. Each case is initially placed in one of k clusters, cases are then moved between clusters if it minimises the differences between cases within a cluster. Depending on the computational capability of the PC-acquisition system and subject to any requirement for real-time analysis one of the aforementioned processes may be adopted.

In addition to the embodiment set out above, further variants having different MEA 3 arrangements are contemplated, some of which are set out below:
(1) SINGLE WELL, MULTIPLE CHAMBER ENVIRONMENT MEASURES—has sensors incorporated into the chamber apparatus to include simultaneous measurement and control of the culture environment (controlled perfusion, temperature, pH sensors).
(2) SINGLE WELL, MULTIPLE CHAMBER ENVIRONMENT MEASURES, MULTIPLE CELL PHYSIOLOGY MEASURES—as in (1) with integrated sensors to enable measurement of other cell functions such as intracellular calcium levels, lactate production etc.
(3) MULTI-WELL, MULTI-CHANNEL SYSTEM—instead of a single well format, 96wells are formed and data retrieved from multiple microelectrodes in each well.
(4) MULTI-WELL, MULTI-PARAMETER SYSTEM—combination of (1) and (3) producing a drug screening device. A completely controlled multiwell assay system capable of controlled delivery of drug and fully automated data capture and analysis
(5) MULTI-WELL, MULTI-PARAMETER SYSTEM, MULTIPLE CELL PHYSIOLOGY MEASURES. Combination of (2) and (3) to allow integrated analysis of many cell functions in many different assays.

Figure 4:
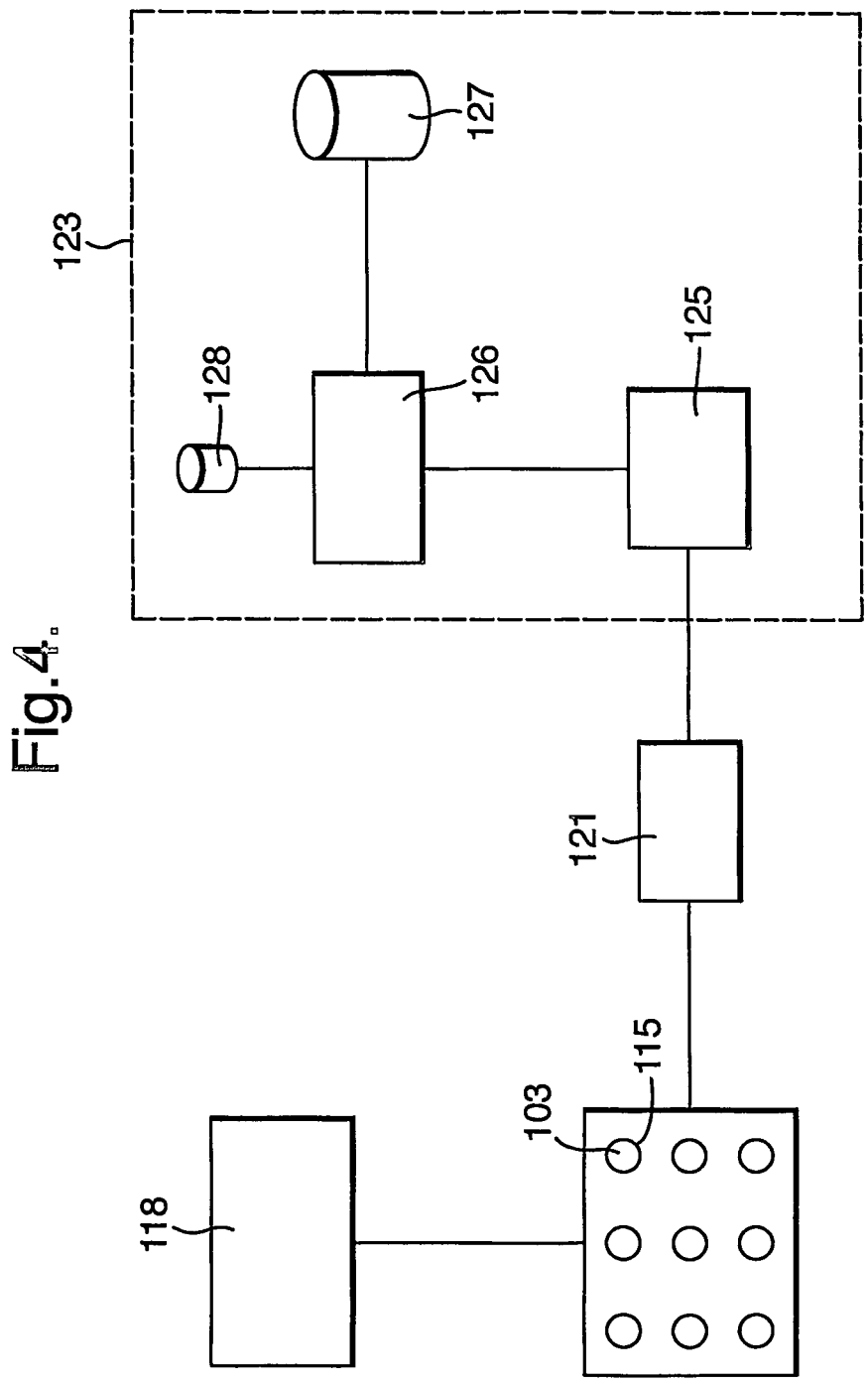
FIG. 4 is a diagrammatic view of a sensor in accordance with a further aspect of the invention.

In accordance with a further embodiment of the invention, there is provided a sensor for the detection of compounds such as environmental toxins. FIG. 4 shows a schematic diagram of the sensor in which the cellular network is provided by a culture of cells derived from a species that is subject to a threat or a species whose response to a toxin, for example, may be extrapolated to another species such as humans. For example, the cellular network may comprise scallop heart cells.

The sensor 101 includes a plurality of chambers 117 each capable of housing an MEA 103. A perfusion system 118 permits the delivery of samples to be tested, for example a test sample derived from river water, to each MEA 103. The MEA 103 is as previously described in relation to the first embodiment in that it has a plurality of electrodes 107 arranged to contact the cellular network, in use. Electrical signals output from the electrodes 107 pass via an interconnect 119 to the amplifier unit 121 where the output is amplified. The amplifier unit 121 is a multichannel device capable of providing a gain of around 1000 to each channel. Typically, sufficient channels are available to allow each electrode 107 of the MEA 103 to be mapped to a channel. Depending on the configuration of the MEA 103 there may be need for more or less channels for satisfactory data collection. The amplifier unit itself is interfaced to a PC-based data acquisition system 123. The PC system 123 incorporates an Analogue to Digital conversion card 125 coupled via PCI bus to a central processor unit 126. The card 125 provides the external connections necessary to interface the analogue output of the amplifier 121 to the acquisition system 123. The card 125 is capable of sampling the amplified channel data from the amplifier unit 121 at up to 50 kHz/channel. The actual rate is determined by reference to the nature of cellular network and the resolution required to identify features of interest The central processor unit 126 carries out instructions provided by software and/or firmware necessary to analyse the digital data. The data may be analysed in real time as events occur on the MEA 103 or retrieved from a storage device 127 such as a hard disk. In the former case, the storage device 127 may still be utilised to archive the data for later repeated or further analysis. The ability to proceed with real time as opposed to or off-line analysis will in some part depend on the rate at which data is generated and the storage capacity of the system 123.

The software and/or firmware includes a library 128 of feature sets corresponding to experimental or otherwise derived responses to a particular toxin or toxins for a particular cellular network under threat As such, the sensor 101 typically is required to perform an identification and preferably classification function in relation to a pre-defined set of feature sets, i.e. there is no requirement for the sensor 101 to identify every compound that is present in the sample only those whose effect might be toxic to the species under threat. Depending on the particular species under investigation, different libraries of feature sets may be loaded into the sensor 101. Conveniently, the sensor 101 is provided with software specific to the species with which a user is intending to work. Such software will contain the libraries as integrated portions of the software or as user loadable software modules. For example, accumulation of toxins in shellfish represents a growing problem. Two toxins are of particular importance because of their profound effects on the human nervous system. These are amnesiac shellfish poisoning (ASP) and paralytic shellfish poisoning (PSP) toxins. Ingestion of large doses of these toxins can result in death.

Figure 5:
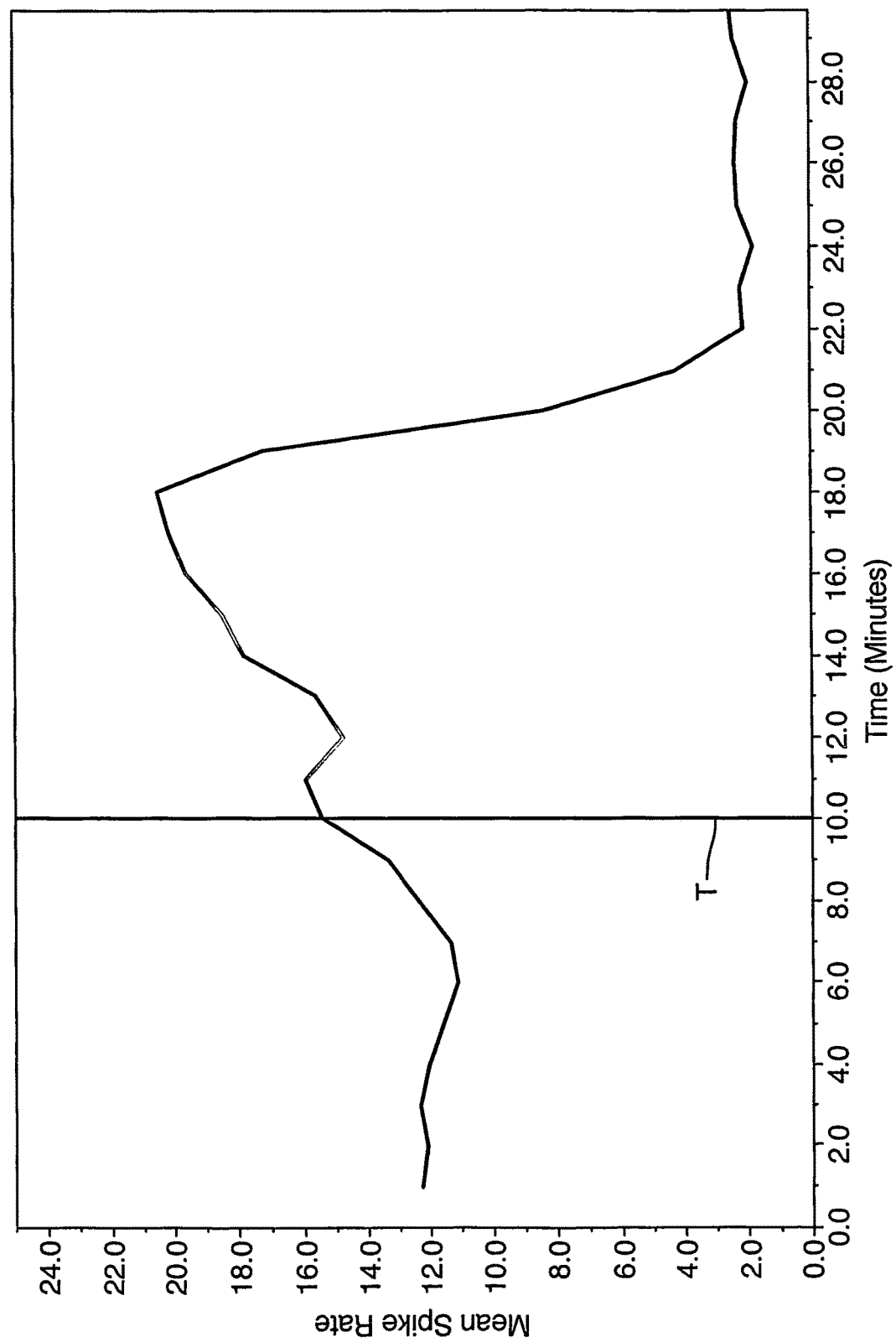
FIG. 5 is a graph illustrative of a response to a compound output of the sensor of FIG. 4.

Taking ASP poisoning as an example of the use of the sensor 101, it is known that the toxin primarily involved in ASP is domoic acid. Accordingly, before the sensor 101 may be utilised to detect the presence or otherwise of a particular toxin, it is necessary to provide a feature set for inclusion in the library 128 for subsequent use in the sensor. The creation of such a feature set or vector can be carried out using the system—described in the first embodiment. In the case of ASP, as has been indicated, the primary toxin is domoic acid. Thus, a network of cortical neurone cells from a mouse is applied to an MEA. The MEA is then placed within the well 115 and as has been described previously, the electrical response of the network to the addition of the compound, in this case domoic acid is extracted by the electrodes 107, amplified and the active channels identified and the relevant data captured. This data is then analysed, again as has been described above and in the case of domoic acid it is found that one particularly useful feature indicative of domoic acid is Mean Spike Rate (MSR). FIG. 5 is a graph illustrating the mean spike rate from rat cortical neurone culture when exposed to domoic acid of 100 nM concentration at 10 minutes from the start of the data as indicated by the heavy line T. This response is then parameterised and stored in a file for inclusion in a software library of features.

Subsequently, a sensor 101 is used to determine the presence or otherwise of ASP in a sample of shellfish. The sensor 101 incorporates storage for a library of feature sets or vectors indicative of the responses to particular toxins realised by particular species. The library may be downloaded to the sensor such that it is held on a hard disk or other storage media 127 or it may be accessed via a network connection to a database. In one particular variant, the library is stored in an integrated circuit formed on the MEA 103 itself. Thus, by means of colour coding or another indicia, an appropriate MEA 103 is selected having the requisite prestored library of feature sets or vectors applicable to a particular species under study. The integrated circuit is provided with the appropriate connections to the card edge connector to allow the library to be accessed by the sensor when installed in the receptacle in the well 115.

Either before or after installation in the receptacle 113, a cellular network of rat derived cortical neurone cellular material is deposited on an MEA 103. The MEA 103 is placed within the receptacle 113 in the well 115 of the sensor 101 and a shellfish sample is placed upon the MEA 103. The electrical response of the network to the addition of the compound (in this case the shellfish sample) is extracted by the electrodes 107, amplified and the active channels identified and the relevant data captured. This data is then analysed against a library of feature sets including that obtained for ASP in relation to the MSR feature. If a match with a library response is found, within a predetermined limit of statistical confidence, then a positive result is flagged and an appropriate warning indication is given by the sensor 101 which may be visual, audio or a combination thereof. Where no such response is identified, again with a particular statistical confidence, then no such warning is given merely an indication with a level of confidence that the sample seems to be toxin free. Clearly, further features may exist which are found to correlate strongly with the presence or otherwise of a particular toxin. Such a feature set may be utilised in the analysis of unknown compounds and a match with one or more may be sufficient to cause the sensor to generate a warning indication.

In a further embodiment of the invention, the PC system 23 may be utilised as a measuring tool. Thus, the system 23 may be utilised to assess the physical and/or chemical characteristics of a known compound. For example, it has been recognised that the response of the system 23 to a particular compound may depend on the concentration of that compound. By establishing a library of features or feature set indicative of particular concentration levels at predetermined levels of statistical confidence, the concentration of a particular known compound may be identified. It will be further appreciated that the measurement tool may be integrated with the identification and classification function such that an initially unknown compound may be both identified and particularised in terms of its physical/chemical properties.

It will be recognised by those skilled in the art that a number of factors will impinge on the statistical confidence a user may have in the results of analysis using the method and apparatus of the invention. A quantification of the impact such factors might have may be incorporated in the statistical level of confidence applied to the results of a particular analysis. In order to minimise such effects, steps may be taken to utilise features that are normalised relative to a control. Alternatively, the minimum concentration to produce a significant response could be employed. Additionally, the response of the system may depend on the proximity of each cell to its nearest electrode. This may require the use of features that are independent of absolute amplitude, such as beat rate.

The invention claimed is:
1. A compound analysis system, the system comprising:
a micro-electrode array comprising a bio-compatible substrate, an isolated, living biological sample comprising an electrically active cellular network, and a plurality of electrodes, the array additionally comprising a plurality of electrically active channels as determined by said electrodes being in contact with cells of the electrically active cellular network;

a multi-channel amplifier coupled to said electrodes;

a processor and a memory operatively connected to said amplifier and operable to record changes in a plurality of features of the living biological sample in response to exposure to a compound, the plurality of features comprise spike speed and one or more other features comprising changes to the temporal and spatial pattern of recorded spikes, the processor and memory further operable to determine a multi-dimensional vector comprising one dimension for each of the plurality of features, wherein said memory contains a library of vectors indicative of responses to known compounds and the processor and memory is further operable to compare the derived multi-dimensional vector to the library of vectors to identify the compound.

2. The compound analysis system according to claim 1, wherein the plurality of features are selected from the group consisting of: instantaneous spike rate, instantaneous spike rate variability, spike speed variability, peak level, trough level, peak-to-trough level, absolute peak level, rise time to 10%, rise time to 20%, recovery time to 10%, recovery time to 20%, peak-to-trough time, qt time, profile decay rate, absolute profile area, profile rise area, absolute profile recovery area, profile turning moment, absolute profile centre of gravity, absolute profile radius of gyration, amplitude variance, maximum spectral value, frequency of maximum spectral value, amplitude variance in frequency band 1 between 0-250 hz, amplitude variance in frequency band 2 between 250-500 hz, amplitude variance in frequency band 3 between 500-750 hz, amplitude variance in frequency band 4 between 750-1000 hz, ratio of the amplitude variance in the frequency band 2 and the frequency band 1, ratio of the amplitude variance in the frequency band 3 and the frequency band 2, amplitude correlation coefficient, amplitude skewness (normalized), amplitude kurtosis (normalized), entropy of profile, entropy of absolute profile, maximum wavelet transform coefficient, scale change of wavelet transform coefficient, variance of wavelet transform, wavelet transform transfer coefficient, variance of wavelet transform ridge values, and wavelet transform transfer coefficient ridge values.

3. The compound analysis system according to claim 1, wherein the vectors determined for each channel include redundant features.

4. The compound analysis system according to claim 1, wherein each vector is subject to cluster analysis.

5. The compound analysis system of claim 4, wherein said cluster analysis is selected from a polythetic agglomerative cluster analysis, a k-means cluster analysis, or an iterative relocation cluster analysis.

6. The compound analysis system of claim 1, wherein the analyzer comprises:

a transducer configured to convert the electrical output into a machine readable form.

7. The compound analysis system of claim 1, wherein the compound comprises an environmental toxin.

8. The compound analysis system of claim 1, wherein the electrically active cellular network comprises cardiomyocytes, muscle cells, or neuronal cells.

9. The compound analysis system of claim 1, wherein the vector comprises dimensions representative of local and global features across the channels.

10. The compound analysis system of claim 2, wherein the vector dimensions correspond to measurements comprising mean spike rate, spike rate variability, spike speed, and peak level.

* * * * *